United States Patent [19]

Huff et al.

[11] 4,200,653

[45] Apr. 29, 1980

[54] INSECTICIDAL COMPOUND AND METHOD OF USE

[75] Inventors: Roger K. Huff, Wokingham; David D. Evans, Binfield; Nicholas H. Anderson, Wokingham, all of England

[73] Assignee: Imperial Chemical Industries Limited, London, England

[21] Appl. No.: 947,701

[22] Filed: Sep. 29, 1978

[51] Int. Cl.² .................. A01N 9/20; C07C 127/19
[52] U.S. Cl. ................... 424/322; 260/553 A
[58] Field of Search ............. 260/553 A, 554; 424/322, 323

[56] References Cited

U.S. PATENT DOCUMENTS

| | | | |
|---|---|---|---|
| 3,957,867 | 5/1976 | Bukowick | 260/553 A |
| 4,107,294 | 8/1978 | Chauthani | 424/322 |

OTHER PUBLICATIONS

Chemical Abstracts, vol. 76 (1972), p. 85578m.

*Primary Examiner*—V. D. Turner
*Attorney, Agent, or Firm*—Cushman, Darby & Cushman

[57] ABSTRACT

Compounds of the formula

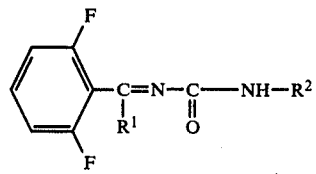

wherein $R^1$ is an alkenyloxy group; an alkoxy group optionally substituted by one or more phenyl radicals or atoms of fluorine, chlorine, bromine or iodine; a phenoxy group optionally substituted by one or more lower alkyl or lower alkoxy groups or atoms of fluorine, chlorine, bromine or iodine; an alkylthio group optionally substituted by one or more phenyl radicals; a phenylthio radical optionally substituted by one or more atoms of fluorine, chlorine, bromine or iodine, or lower alkyl, lower alkoxy, of lower haloalkyl radicals; or an amino radical optionally substituted by one or two alkyl radicals, each of which may optionally be substituted by one or more alkoxy radicals or phenyl radicals; and $R^2$ is a phenyl radical optionally substituted by one or more atoms of fluorine, chlorine, bromine or iodine or by one or more lower haloalkyl radicals, or by one or more phenoxy radicals optionally substituted by one or more atoms of fluorine, chlorine, bromine, or iodine, or by one or more lower haloalkyl groups. The compounds are useful for controlling insect pests.

6 Claims, No Drawings

INSECTICIDAL COMPOUND AND METHOD OF USE

This invention relates to chemical compounds useful in the control of pests, particularly insect pests, to compositions containing the compounds, and to methods of preparing the compounds.

According to the present invention there are provided compounds of the formula (I):

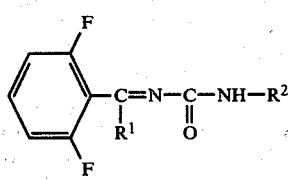

wherein $R^1$ is an alkenyloxy group; an alkoxy group optionally substituted by one or more phenyl radicals or atoms of fluorine, chlorine, bromine or iodine; a phenoxy group optionally substituted by one or more lower alkyl or lower alkoxy groups or atoms of fluorine, chlorine, bromine or iodine; an alkylthio group optionally substituted by one or more phenyl radicals; a phenylthio radical optionally substituted by one or more atoms of fluorine, chlorine, bromine or iodine, or lower alkyl, lower alkoxy, or lower haloalkyl radicals; or an amino radical optionally substituted by one or two alkyl radicals, each of which may optionally be substituted by one or more alkoxy radicals or phenyl radicals; and $R^2$ is a phenyl radical optionally substituted by one or more atoms of fluorine, chlorine, bromine or iodine or by one or more lower haloalkyl radicals, or by one or more phenoxy radicals optionally substituted by one or more atoms of fluorine, chlorine, bromine, or iodine, or by one or more lower haloalkyl groups.

By the terms lower alkyl, lower alkoxy, and lower haloalkyl groups, we mean groups in which the alkyl moiety contains from 1 to 6 carbon atoms.

Examples of compounds according to the invention include those of the foregoing formula (I) in which the group $R^2$ is a 3,4-dichlorophenyl or 4chloro-3-trifluoromethyl phenyl radical, and $R^1$ is an alkoxy group of 1 to 12 carbon atoms.

Particular examples of compounds provided by the invention are listed in Table I below:

TABLE I

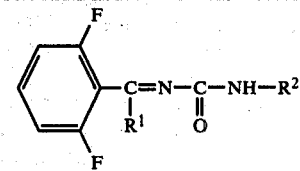

| Compound No. | $R^1$ | $R^2$ | Melting Point °C. |
|---|---|---|---|
| 1 | $OC_2H_5$ | 3,4-dichlorophenyl | Oil (Z:E = 60:40) |
| 2 | $OC_2H_5$ | " | 96 (Pure Z) |
| 3 | $OCH_3$ | " | 128 |
| 4 | $OCH(CH_3)_2$ | " | |
| 5 | $OnC_{11}H_{23}$ | " | |
| 6 | $OCH_2C_6H_5$ | " | |
| 7 | $OnC_6H_{13}$ | " | |
| 8 | $OCH_2CF_3$ | " | |
| 9 | $OCH(CF_3)_2$ | " | 150 |
| 10 | $OCH_2CH=CH_2$ | " | |

TABLE I-continued

| Compound No. | $R^1$ | $R^2$ | Melting Point °C. |
|---|---|---|---|
| 11 | $OC_6H_5$ | " | 195 |
| 12 | $SC_4H_9n$ | " | |
| 13 | 4-chlorophenylthio | " | 165 |
| 14 | $SCH_2C_6H_5$ | " | 89 |
| 15 | $NHCH_3$ | " | 142 |
| 16 | $N(CH_3)_2$ | " | 133 |
| 17 | $NHCH_2CH_2OC_2H_5$ | " | 107 |
| 18 | $NHCH(CH_3)_2$ | " | 163 |
| 19 | $NHC_2H_5$ | " | 124 |
| 20 | $OC_2H_5$ | 4-chloro-3-trifluoromethylphenyl | |
| 21 | $OC_{11}H_{23}n$ | 4-chloro-3-trifluoromethylphenyl | |
| 22 | $OC_2H_5$ | 4-(2-chloro-4-trifluoromethylphenoxy)-phenyl | 110–113 |

The compounds of the invention are capable of existing in two different geometrically isometric forms, depending upon the spatial disposition of the substituent groups about the $>C=N-$ bond in the molecule. Following conventional chemical nomenclature, the two forms of a particular compound are designated as the E and the Z isomers of the compound. Referring to compound no. 1 of Table I, the E and Z forms are shown below by way of example.

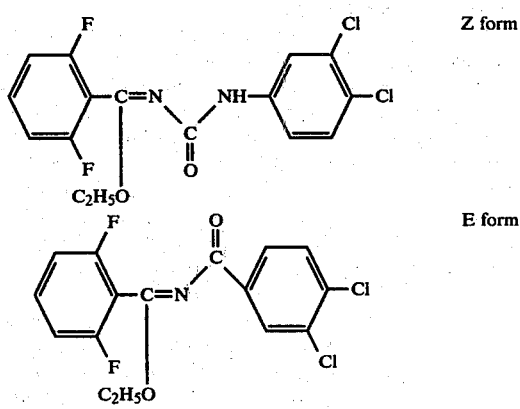

In Table I, compounds 1 and 2 have the same molecular formula. Compound 1 is a mixture of E and Z forms in the ratio shown and compound Z is the pure Z isomer.

Depending upon the process chosen for preparing a particular compound, or on the way in which the conditions for a particular process are varied, either of the E and Z forms may be obtained, or a mixture of the two. The isomers, having different physical properties, may be separated by physical processes known in the chemical art. Both isomers of a particular compound have biological activity, but the biological effects of the isomers may not be completely identical in every case. The compounds in Table I are mixtures of E and Z forms unless otherwise specified.

The compounds of formula I may be used to combat and control infestations of insect pests particularly lepidopterous and coleopterous insects. The insect pests which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals. Thus the compounds may be used to control mosquito larvae and the larvae of the common housefly. The compounds may also be effective in controlling infestations of Coleoptera and Diptera by causing the laying of infertile eggs.

In order to apply the compounds to the locus of the pests they are usually formulated into compositions which include in addition to the insecticidally active ingredient or ingredients of formula I suitable inert diluent or carrier materials, and/or surface active agents. The compositions may also comprise another pesticidal material, for example another insecticide or acaricide, or a fungicide, or may also comprise a insecticide synergist, such as for example dodecyl imidazole, safroxan, or piperonyl butoxide.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material for example pumice.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example, cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, butylnaphthalene sulphonate, and a mixture of the sodium salts of diisopropyl- and triisopropylnaphthalene sulphonates. Suitable agents of the non-ionic type include for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents. Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydro furfuryl alcohol (THFA).

The compositions to be used as sprays may also be in the form of aerosols wherein the formulation is held in a container under pressure in the presence of a propellant such as fluorotrichloromethane or dichlorodifluoromethane. The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogeneous for a sufficient time to enable them to be applied by conventional spray equipment. The concentrates may contain 10-85% by weight of the active ingredient or ingredients. When diluted to form aqueous preparations, such preparations may contain varying amounts of the active ingredient depending upon the purpose for which they are to be used.

For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying. The rate of application will depend upon factors such as the insect species to be controlled but in general a rate of from 5 to 1000 g per hectare will be appropriate.

The compositions of the invention are very toxic to a variety of insect pests, including, for example, the following:
*Plutella maculipennis* (diamond black moth, larvae)
*Phaedon cochleariae* (mustard beetle)
Trialeuroides spp. (white flies)
*Spodoptera littoralis* (cotton leaf worm)
Compounds of the invention wherein the group $R^1$ is an alkenyloxy, alkoxy, or phenoxy group may be prepared by reacting a 1,3,5-oxadiazine derivative (II) with the appropriate alkenol, alkanol, or phenol.

The reaction is illustrated below for the case where the alkanol is ethanol.

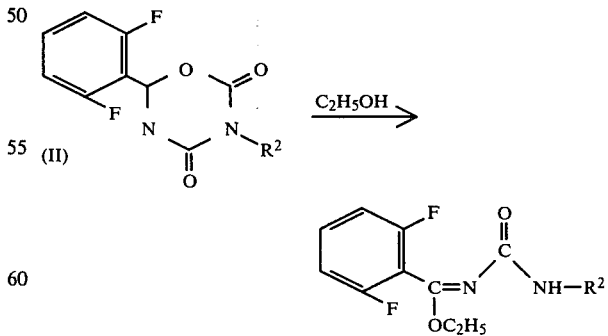

Compounds according to the invention wherein the group $R^1$ ia an alkylthio or phenylthio group may be prepared in the same way by reacting the appropriate 1,3,5-oxadiazine derivative (II) with the appropriate alkanethiol or thiophenol.

Compounds according to the invention in which the group $R^1$ is an amino group or an amino group substituted by one or two alkyl groups may be prepared by reacting the appropriate 1,3,5-oxadiazine (II) with ammonia or with the appropriate mono- or di-alkylamine. The 1,3,5-oxadiazine derivatives (II) may be prepared as described in German Offenlegungschrift No. 2732115. The reaction with the alkenol, alkanol, phenol, alkanethiol, thiophenol, ammonia, or amine may if desired be carried out in a solvent inert to the reactants. It may be convenient to carry out the reaction by treating the oxadiazine with an excess of the other reactant as the solvent. The reaction may if desired be accelerated by heating.

In an alternative method of preparation, compounds in which $R^1$ is an alkoxy or alkenyloxy group may be prepared by the reaction scheme outlined below:

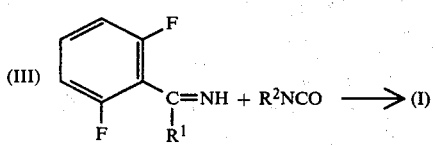

In this scheme, the imidate ester (III), wherein $R^1$ is an alkenyloxy, or alkoxy group, is reacted with the appropriate isocyanate $R^2NCO$ to give the compounds of the invention. The imidate esters and the isocyanates $R^2NCO$ may be prepared by standard methods well known in the chemical art. Compounds wherein the group $R^1$ is an alkyl-thio group may also be prepared by the last foregoing reaction scheme.

The invention is illustrated by the following Examples in which all the parts are by weight and all temperatures in degrees Centigrade unless otherwise specified.

EXAMPLE 1

This Example illustrates the preparation of compound no. 20 of Table I.

(a) Preparation of ethyl 2,6-difluorobenzimidate 2,6-Difluorobenzamide (1.56 g) in methylene chloride was added to triethyloxonium fluoborate (1.9 g) in methylene chloride and the mixture stirred for 24 hours. The solution was then washed three times with cold sodium carbonate solution and dried over sodium sulphate. The methylene chloride solution was evaporated to yield an oil. This was mixed with chloroform and the solution filtered from insoluble material. Evaporation of the chloroform gave the ethyl 2,6-difluorobenzimidate as a mobile oil.

(b) Preparation of compound no. 20

The product from paragraph (a) above (0.33 g) in dry ether was added slowly to a stirred solution of 4-chloro-3-trifluoromethylphenyl isocyanate (0.28 g) in dry ether. The mixture was stirred for several hours and then left at room temperature for 3 days. The solvent was then removed and the residue recrystallised from hexane to give compound no. 20 with a melting point of 109° C.

EXAMPLE 2

This Example illustrates the preparation of compound no. 2 of Table I (i.e. the pure Z isomer of compound no. 1).

3-(3,4-Dichlorophenyl)-5-(2,6-difluorophenyl)-3,4-dihydro-2-H-1,3,5-oxadiazin-2,4-dione (0.6 g) prepared as described in Example 3 of West German Offenlegungschrift No. 2732115, was heated under reflux with ethanol (15 ml) for 2 hours, when all the solid had dissolved. Water was then added until the solution became slightly turbid and the solution left to stand. The crystals which separated were collected and identified as compound no. 2, having a melting point of 96° C. The nuclear magnetic resonance spectrum of the product was in agreement with the structure assigned.

EXAMPLE 3

This Example illustrates the insecticidal activity of compounds according to the invention.

The compounds of the invention were formulated for test by dissolving a sample of each compound in the minimum amount of a mixture of 1 part by volume of ethyl alcohol and 1 part by volume of acetone, and then diluting the solution so obtained with water to give a solution having a concentration of 1000 parts per million. These solutions were then used in tests on mustard beetle (*Phaedon cochleariae*) and cotton leaf worm (*Spodoptera littoralis*). These tests were carried out as follows:

Mustard Beetle

Pots containing mustard cotyledons are sprayed to run-off with the spray solution described above. When dry the sprayed foliage is fed to mustard beetle larvae (4th instar stage) kept in Petri dishes containing filter paper (10 larvae per dish). After 48 hours the filter paper is changed and the dead larvae counted. The larvae are fed again with a single unsprayed leaf and further mortality counts made at 6 and 12 days.

Cotton Leaf Worm Test

The test is similar to that described for the mustard beetle above, with the following differences:

Cabbages are used as the test plants and 5 larvae instead of 10 are used. Mortality counts are made at 48 hours at which stage the filter paper is removed and the larvae fed on an untreated artificial diet. A further count is made at 6 days. Two replicates are used in all tests.

The results are given below in Table II.

In the Table, the results given are expressed on a scale of 0 to 3, corresponding to the following ranges of percentage kill:

| Scale Figure | Percent Kill |
| --- | --- |
| 0 | Less than 30 |
| 1 | 30–49 |
| 2 | 50–90 |
| 3 | 90–100 |
| 0 | |

A dash (—) means that no test was carried out.

| Compound No. Table | Test Species | |
| --- | --- | --- |
| | *Spodoptera Littoralis* | *Phaedon Cochleariae* |
| 1 | — | 3 |
| 3 | — | 3 |
| 4 | — | 3 |
| 5 | — | 3 |
| 6 | — | 3 |
| 8 | — | 3 |
| 9 | — | 2 |
| 10 | — | 3 |
| 11 | — | 3 |
| 13 | — | 3 |
| 14 | — | 3 |
| 15 | — | 3 |

| | | |
|---|---|---|
| -continued | | |
| 16 | — | 3 |
| 17 | — | 3 |
| *18 | 3 | — |
| 19 | 2 | 3 |

*Tested at a concentration of 500 parts per million.

Experiments were carried out in which the compounds of the invention were tested side by side on the foregoing insect species with the known insecticidal compound difluobenzuron, having the following formula:

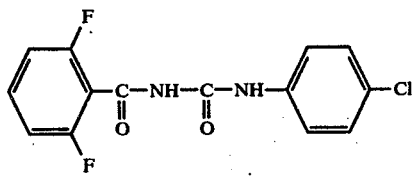

In these tests, a number of the compounds of the invention were substantially more effective than difluobenzuron. Particularly insecticidally active compounds include numbers 1, 3, 20 and 22 of Table I.

We claim:

1. A compound of the formula (I):

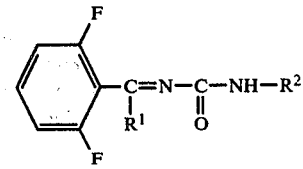

wherein $R^1$ is alkyloxy; alkoxy of 1–12 carbons, unsubstituted or substituted by phenyl, fluorine, chlorine, bromine or iodine; phenoxy, unsubstituted or substituted by lower alkyl, lower alkoxy, fluorine, chlorine, bromine or iodine; alkylthio of up to 4 carbons, unsubstituted or substituted by phenyl; phenylthio, unsubstituted or substituted by fluorine, chlorine, bromine, iodine, lower alkyl, lower alkoxy or lower haloalkyl; or amino, unsubstituted or substituted by from one to two unsubstituted alkyl of up to 3 carbons or by such alkyl substituted by ethoxy or phenyl; and $R^2$ is an unsubstituted phenyl, a phenyl substituted by fluorine, chlorine, bromine, iodine, lower haloalkyl, unsubstituted phenoxy or phenoxy substituted by fluorine, chlorine, bromine, iodine, or lower haloalkyl.

2. A compound according to claim 1 wherein $R^1$ is alkoxy of 1 to 12 carbon atoms, and $R^2$ is 3,4-dichlorophenyl or 4-chloro-3-trifluoromethylphenyl.

3. A compound according to claim 1 in the form of an isomer of either the E or the Z configuration and substantially free from contamination by the other isomer.

4. An insecticidal composition comprising an insecticidally effective amount of a compound according to claim 1 in association with an inert diluent or carrier material.

5. A method of combating insect pests in which an insecticidally effective amount of a composition according to claim 4 is applied to the pests or the locus of the pests.

6. A method according to claim 5 wherein the locus of the pests are growing plants liable to infestation by the pests.

* * * * *